United States Patent [19]

Laver

[11] Patent Number: Plant 7,326

[45] Date of Patent: Sep. 18, 1990

[54] ROSE PLANT—LAVJACK VARIETY

[75] Inventor: Keith Laver, Caledon East, Canada

[73] Assignee: The Conard-Pyle Company, West Grove, Pa.

[21] Appl. No.: 343,869

[22] Filed: Apr. 27, 1989

[51] Int. Cl.[5] ..... A01H 5/00

[52] U.S. Cl. ..... Plt./10

[58] Field of Search ..... Plt. 10, 10.1

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which forms abundantly and continuously highly attractive fully double blossoms. The blossoms exhibit a very stable orange-red coloration and the plant forms small foliage. The new variety is well suited for greenhouse production as a pot plant and is not particularly affected by crytogamic diseases. The blossoms are long lasting on the plant and the petals drop off cleanly.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Julie Ann variety (non-patented in the United States). The male parent (i.e., the pollen parent) of the new variety was the Potluck variety (non-patented in the United States). The parentage of the new variety can be summarized as follows:

Julie Ann × Potluck.

The seeds resulting from the above pollination were sown and plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive fully double long lasting blossoms which are of a very stable orange-red coloration,
(b) forms small foliage,
(c) exhibits a bushy growth habit,
(d) exhibits good disease resistance, and
(e) is well-suited for greenhouse production as a pot plant.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including cuttage, etc. The characteristics of the new variety have been found to be strictly transmissible by such asexual propagation from one generation to another.

The new variety has been named the Lavjack variety.

BRIEF DESCRIPTION OF THE PHOTOGRAPHS

The accompanying photographs show as nearly true as it is reasonably possible to make the same, in color illustrations of this character, typical specimens of the new variety. The rose plants of the new variety illustrated herein were one year of age and were observed during February while grown in 4-inch (i.e., 10 cm.) pots in a greenhouse at West Grove, Pa.

FIG. 1 at the far left illustrates a specimen of a main branch; at the center beginning at the top (a) a specimen of a leaf with five leaflets showing the under surface wherein the lower leaflet pair appears to be incomplete, (b) a specimen of a leaf with seven leaflets showing the under surface, (c) a specimen of a leaf with seven leaflets showing the under surface, (d) a specimen of a leaf with three leaflets showing the upper surface, and (e) a specimen of a leaf with seven leaflets showing the upper surface; at the center right specimens of three blossoms in various stages in opening; and at the far right beginning at the top (a) a specimen of a bud at the opening of the sepals, (b) a specimen of a flowering shoot with unopened buds, (c) a specimen of a flowering bud, and (d) a specimen of a blossom in the early opening stage.

FIG. 2 illustrates a fully grown plant of the new variety while blossoming is in progress.

DETAILED DESCRIPTION

Figure 1:
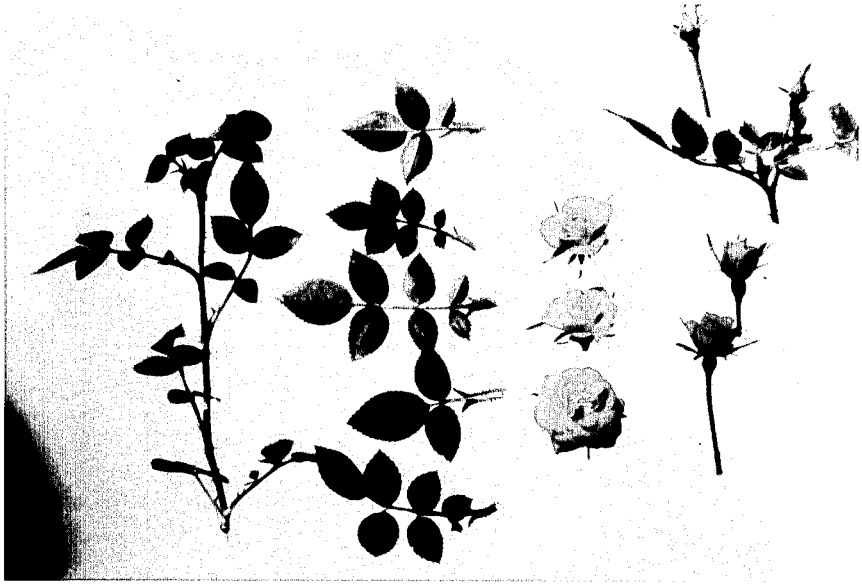
Figure 2:
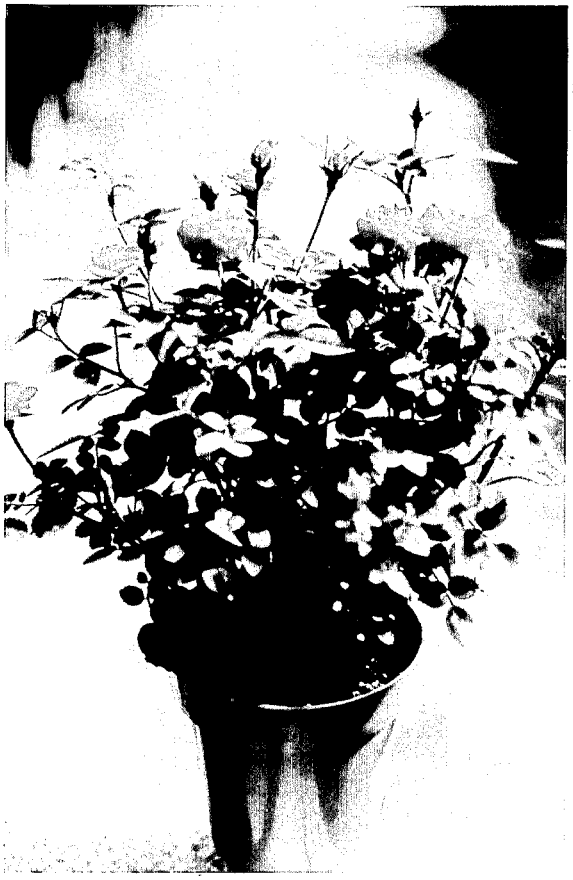

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety during February while grown in 4-inch (i.e., 10 cm.) pots in a greenhouse at West Grove, Pa.

Class: Miniature.

Plant:

*Height.*—Approximately 18 to 20 cm. on average when grown in a 4-inch pot.

*Habit.*—Bushy.

Branches:

*Color.*—Young stems: reddish green. Adult wood: medium green, Green Group 137A.

*Thorns.*—Size: small. Quantity: very abundant. Color: reddish.

Leaves:

*Petioles.*—Upper surface: striped reddish brown on young wood and medium to dark green with glandular edges on adult wood. Under surface: medium green with a few tiny prickles.

*Stipules.*—Adnate, pectinate, narrow and linear.

*Leaflets.*—Number: 3, 5 (most often), and 7, sometimes the lower leaflet pair is incomplete. Shape: elliptic. Serration: single and regular. Texture: firm (consistent). General appearance: dull foliage which often is not very dense. Color (young foliage): Upper surface: Green Group 137A stained with reddish coloration coupled with reddish edges. Under surface: Green Group 137C. Color (adult foliage): Upper surface: dark green, Green Group 139A. Under surface: medium green, Green Group 137C.

Inflorescence:

Number of flowers.—Approximately 1 to 7 per stem, with 3 to 5 per stem being more frequent.

*Peduncle.*—Light green, rigid, straight, it bears many reddish prickles, its length is approximately 3.5 cm. on average.

*Sepals.*—Upper surface: tomentose, and greenish in coloration. Under surface: medium green, and bear numerous tiny reddish appendiculate glands and a few prickles.

*Buds.*—Shape: conical. Length: approximately 1 cm. on average. Size: small. Color upon opening: Upper Surface: Red Group 44A with a greenish central vein. Under surface: Red Group 44B, suffused with Red Group 45A near the edges of the petals, and white at the base.

*Flower.*—Form: cuplike. Diameter: approximately 3.5 cm. on average. Color (when opening begins): Upper surface: capsicum red, Orange-Red Group 33A, turning to Red Group 44A towards the edges of the petals. Under surface: Red Group 44B and suffused and edged with Red Group 45A. The central vein is clearly visible throughout approximately half of the petal length and is whitish in appearance. Color (when blooming): Upper surface: capsicum red, Orange-Red Group 33A, turning to Red Group 44A towards the edges of the petals. Under surface: Red Group 44B and suffused and edged with Red Group 44B. Color (at end of opening):

Upper surface: Red Group 44B suffused with Red Group 44A and having a greenish-white unguis. Under surface: Red Group 44B suffused with Red Group 44A with a whitish central vein on the inner petals. The pistils and stamens are clearly visible at this stage in the center of the bloom. Fragrance: very light and almost nonexistant. Lasting quality: long on the plant. Petal number: approximately 28 to 35 on average plus commonly have 3 to 5 petaloids in the center. Petal texture: firm (consistent). Petal drop: very good. Anthers: strawlike edged with ochre and located above the stigma. Stamen number: approximately 40 to 50 on average. Filaments: yellowish, free standing, of irregular heights. Pistil number: approximately 35 on average. Stigmas: greenish white in coloration. Styles: smaller in size than the filaments, bundled together at the base, of irregular heights, and greenish-white in coloration. Receptacle: medium green, bears numerous prickles and some pediculate glands, and in longitudinal section it is in the shape of a pitcher.

Development:

*Vegetation.*—Very vigorous.

*Blooming.*—Abundant and continuous.

*Aptitude to bear fruit.*—None.

*Resistance to diseases.*—Good.

I claim:

1. A new and distinct variety of Miniature rose plant characterized by the following combination of characteristics:

(a) forms in abundance on a continuous basis attractive fully double long lasting blossoms which are of a very stable orange-red coloration, (b) forms small foliage, (c) exhibits a bushy growth habit, (d) exhibits good disease resistance, and (e) is well suited for greenhouse production as a pot plant;

substantially as herein shown and described.

* * * * *